United States Patent
Chirichiello

(10) Patent No.: US 9,161,613 B1
(45) Date of Patent: Oct. 20, 2015

(54) TONGUE SCRAPER TOOTHBRUSH SYSTEM

(71) Applicant: Massimo Chirichiello, Eliizabeth, NJ (US)

(72) Inventor: Massimo Chirichiello, Eliizabeth, NJ (US)

( * ) Notice: Subject to any disclaimer, the term of this patent is extended or adjusted under 35 U.S.C. 154(b) by 0 days.

(21) Appl. No.: 13/890,283

(22) Filed: May 9, 2013

Related U.S. Application Data

(60) Provisional application No. 61/810,428, filed on Apr. 10, 2013.

(51) Int. Cl.
*A46B 15/00* (2006.01)
*A61B 17/24* (2006.01)
*A46B 9/04* (2006.01)

(52) U.S. Cl.
CPC ........... *A46B 15/0081* (2013.01); *A61B 17/244* (2013.01); *A46B 9/04* (2013.01)

(58) Field of Classification Search
USPC .................. 15/111, 167.1; 132/309; 606/161; D4/108, 113, 118; D24/147, 149
See application file for complete search history.

(56) References Cited

U.S. PATENT DOCUMENTS

| | | | | | |
|---|---|---|---|---|---|
| 1,495,675 | A | * | 5/1924 | Colt | 132/309 |
| 1,891,864 | A | * | 12/1932 | Barrett | 606/161 |
| 4,610,043 | A | * | 9/1986 | Vezjak | 15/111 |
| 5,350,248 | A | * | 9/1994 | Chen | 401/195 |
| 5,758,380 | A | * | 6/1998 | Vrignaud | 15/106 |
| 7,073,225 | B1 | * | 7/2006 | Ford | 15/167.2 |
| 7,594,293 | B2 | * | 9/2009 | Xi et al. | 15/111 |
| 7,607,189 | B2 | * | 10/2009 | Moskovich | 15/111 |

FOREIGN PATENT DOCUMENTS

JP          2002-159342          *   6/2002

* cited by examiner

*Primary Examiner* — Mark Spisich
(74) *Attorney, Agent, or Firm* — RG Patent Consulting, LLC; Rachel Gilboy

(57) ABSTRACT

A tongue scraper toothbrush system for cleaning teeth and tongue of a user is provided. The tongue scraper toothbrush system comprises a handle having a first end and a second end. A brush head is mounted to the first end of the handle. A tongue scraping device is mounted to the handle. The brush head and the tongue scraping device are alternatingly usable to clean the teeth and tongue of the user.

5 Claims, 2 Drawing Sheets

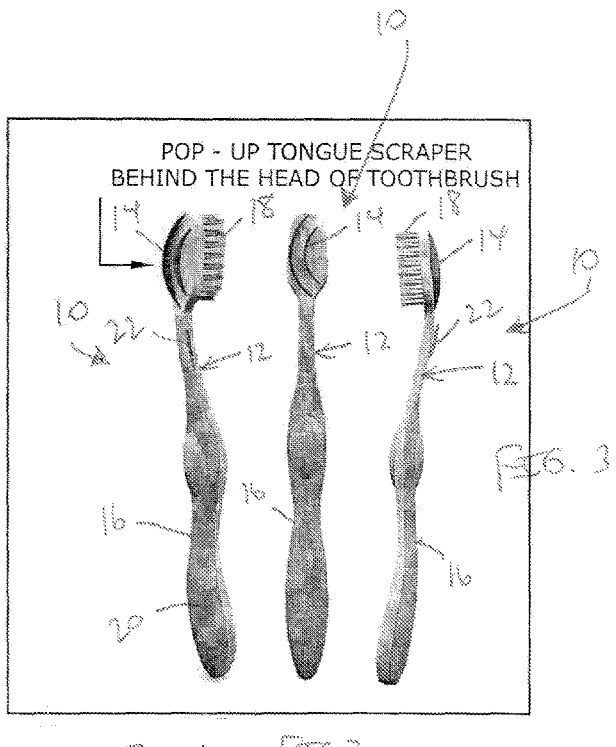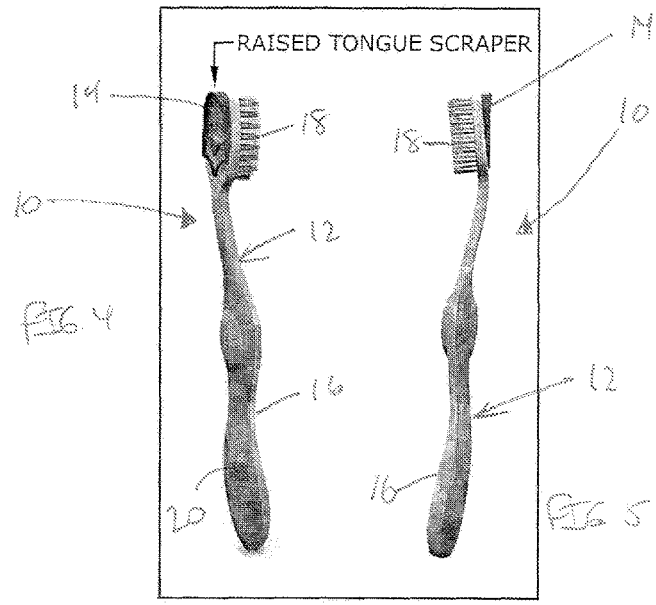

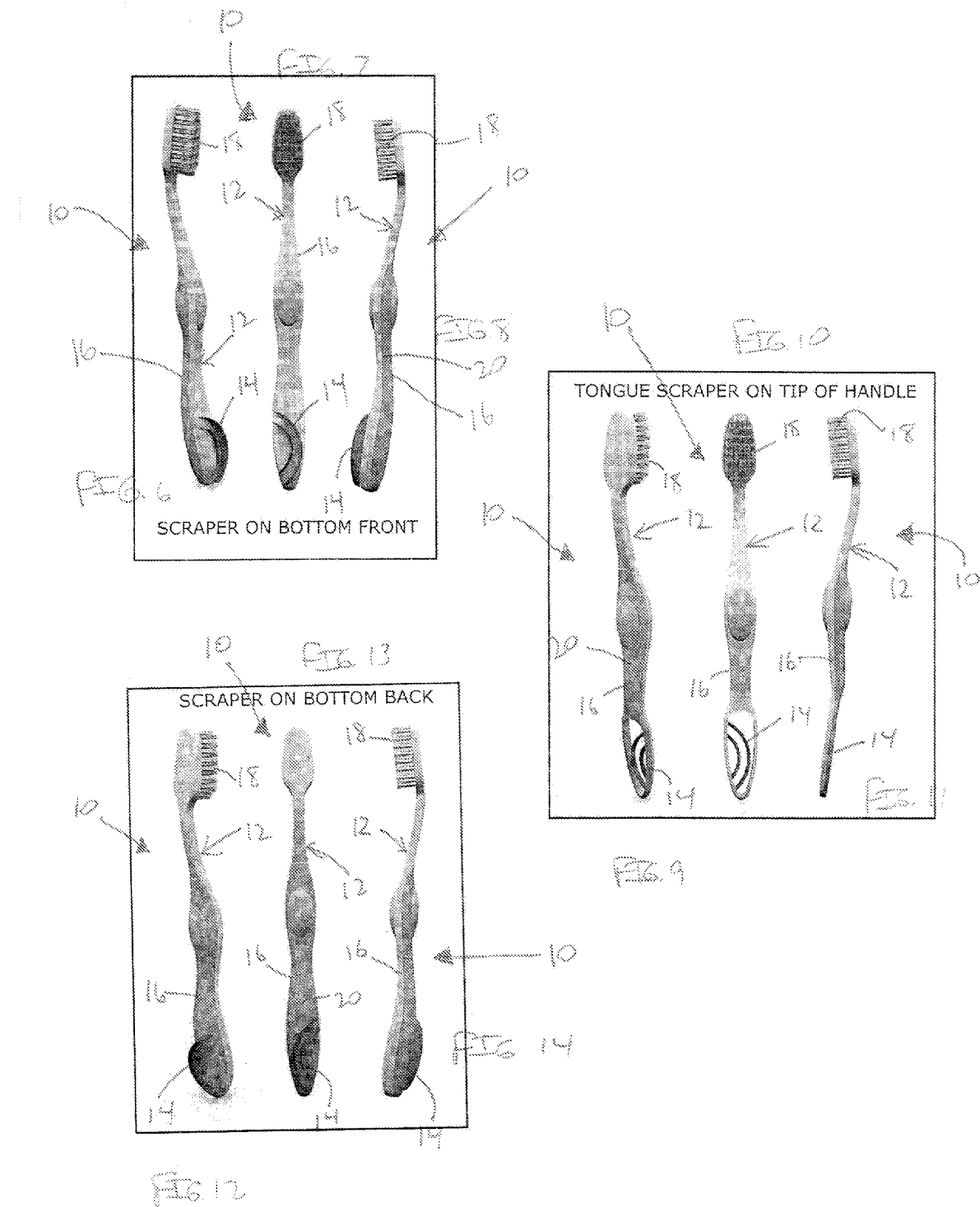

TONGUE SCRAPER TOOTHBRUSH SYSTEM

The present application claims the benefit of priority of provisional patent application Ser. No. 61/810,428, filed on Apr. 10, 2013, entitled "Tongue Scraper Toothbrush".

BACKGROUND OF THE INVENTION

1. Field of the Invention

This invention relates generally to a tongue scraper toothbrush system and, more particularly, the invention relates to a tongue scraper toothbrush system providing a specially designed toothbrush boasting an integrated tongue scraper.

2. Description of the Prior Art

The majority of people are quite diligent at maintaining good oral hygiene, even on the busiest of days. A twice daily regimen, brushing the teeth is often the first activity completed upon waking, and the last before retiring before the evening. In addition to brushing daily, an essential aspect of healthy oral hygiene is the scraping of the tongue. According to dental experts, simple brushing is not always completely effective in eradicating halitosis, or bad breath. The tongue, particularly its remote posterior area, is optimal breeding ground for the germs and bacteria that result in halitosis. As such, the tongue is an extremely important area to keep clean. However, even those most conscientious of their oral health can fail to complete this beneficial activity. Specifically, many simply overlook the necessity of scraping the tongue in the first place, thus fail to engage in this aspect of oral hygiene on a regular basis. Simply stated, while one might regularly remember to purchase toothpaste and a new toothbrush when visiting their local grocery store or pharmacy, many simply forget or overlook the need to purchase tongue scrapers.

SUMMARY

The present invention is a tongue scraper toothbrush system for cleaning teeth and tongue of a user. The tongue scraper toothbrush system comprises a handle having a first end and a second end. A brush head is mounted to the first end of the handle. A tongue scraping device is mounted to the handle. The brush head and the tongue scraping device are alternatingly usable to clean the teeth and tongue of the user.

In addition, the present invention includes a method for cleaning teeth and tongue of a user. The method tongue scraper toothbrush system comprises providing a handle having a first end and a second end, mounting a brush head to the first end of the handle, mounting a tongue scraping device to the handle, and alternatingly using the brush head and the tongue scraping device to clean the teeth and tongue of the user.

The present invention further includes a tongue scraper toothbrush system for cleaning teeth and tongue of a user. The tongue scraper toothbrush system comprises a handle having a first end and a second end. A brush head is mounted to the first end of the handle. A tongue scraping device mounted to the handle. The tongue scraping device initially rests flush with a surface of the handle of the toothbrush with the tongue scraping device activatable with a slide mechanism to raise above the surface of the handle. The brush head and the tongue scraping device are alternatingly usable to clean the teeth and tongue of the user.

BRIEF DESCRIPTION OF THE DRAWINGS

FIG. 1 is a rear perspective view illustrating a tongue scraper toothbrush system, constructed in accordance with the present invention, with a pop-up tongue scraping device positioned behind a head of a toothbrush;

FIG. 2 is a rear view illustrating the tongue scraper toothbrush system of FIG. 1, constructed in accordance with the present invention, with the pop-up tongue scraping device positioned behind the head of the toothbrush;

FIG. 3 is a right side view illustrating the tongue scraper toothbrush system of FIG. 1, constructed in accordance with the present invention, with a pop-up tongue scraping device positioned behind the head of the toothbrush;

FIG. 4 is a rear perspective view illustrating another embodiment of the tongue scraper toothbrush system, constructed in accordance with the present invention, with a raised tongue scraping device positioned behind the head of the toothbrush;

FIG. 5 is a right side view illustrating the tongue scraper toothbrush system of FIG. 4, constructed in accordance with the present invention, with the raised tongue scraping device positioned behind the head of the toothbrush;

FIG. 6 is a front perspective view illustrating still another embodiment of the tongue scraper toothbrush system, constructed in accordance with the present invention, with the tongue scraping device positioned on the bottom front of the toothbrush;

FIG. 7 is a front view illustrating the tongue scraper toothbrush system of FIG. 6, constructed in accordance with the present invention, with the tongue scraping device positioned on the bottom front of the toothbrush;

FIG. 8 is a right side view illustrating the tongue scraper toothbrush system of FIG. 6, constructed in accordance with the present invention, with the tongue scraping device positioned on the bottom front of the toothbrush;

FIG. 9 is a rear perspective view illustrating yet another embodiment of the tongue scraper toothbrush system, constructed in accordance with the present invention, with the tongue scraping device positioned on the tip of the toothbrush handle;

FIG. 10 is a front view illustrating the tongue scraper toothbrush system of FIG. 9, constructed in accordance with the present invention, with the tongue scraping device positioned on the tip of the toothbrush handle;

FIG. 11 is a right side view illustrating the tongue scraper toothbrush system of FIG. 9, constructed in accordance with the present invention, with the tongue scraping device positioned on the tip of the toothbrush handle;

FIG. 12 is rear perspective view illustrating still yet another embodiment of the tongue scraper toothbrush system, constructed in accordance with the present invention, with the tongue scraping device positioned on the bottom back of the toothbrush handle;

FIG. 13 is rear view illustrating the tongue scraper toothbrush system of FIG. 12, constructed in accordance with the present invention, with the tongue scraping device positioned on the bottom back of the toothbrush handle; and FIG. 14 is right side view illustrating the tongue scraper toothbrush system of FIG. 12, constructed in accordance with the present invention, with the tongue scraping device positioned on the bottom back of the toothbrush handle.

DETAILED DESCRIPTION OF THE PREFERRED EMBODIMENTS

As illustrated in FIGS. 1-14, the present invention is a tongue scraper toothbrush system, indicated generally at 10, providing a specially designed toothbrush 12 boasting an integrated tongue scraping device 14. The tongue scraper toothbrush system 10 is preferably constructed from durable plastic materials and features rubber components.

The tongue scraper toothbrush assembly 10 of the present invention includes a toothbrush 12 having a handle 16 and a brush head 18 mounted to the handle 16. The handle 16 has a first end and a second end and the brush head 18 has a plurality of bristles. The plurality of bristles are mounted at the first end of the handle 16 of the toothbrush 12. Preferably, the handle 16 of the toothbrush 12 is an ergonomic, elongated unit configured expressly to comfortably fit in the hand of the user. Preferably manufactured of molded plastic, the handle 16 can further include an integrated, nonskid rubber grip 20, facilitating a firm and comfortable hold during use. The brush head 18 mounted to the first end of the handle 16 of the toothbrush 12 preferably feature short, synthetic fiber bristles having rounded edges for the greatest cleaning comfort and safety. The bristles can be offered in soft, medium and hard textures, thus providing a variety of options for users. As a consideration, the toothbrush 12 itself can be offered in sizes appropriate for use by children.

In addition, the tongue scraper toothbrush system 10 of the present invention includes the tongue scraping device 14 mounted to the handle 16 of the toothbrush 12. The tongue scraping device 14 can be offered in a variety of embodiments. In an embodiment, the tongue scraping device 14 is mounted to the first end of the handle 16 of the toothbrush 12 directly opposite the brush head 18. In another embodiment, the tongue scraping device 14 is mounted to the second end of the handle 16 of the toothbrush 12 on either side of the second end of the handle 16. In any embodiment, the tongue scraping device 14 can either be fixedly raised above a surface of the first end of the handle 16 or the tongue scraping device 14 can initially rest flush with the surface of the handle 16 of the toothbrush 12 and then activated with a slide mechanism 22 to raise the tongue scraping device 14 above the surface of the handle 16 providing easy access prior to use.

In an embodiment of the tongue scraper system 10 of the present invention, the tongue scraping device 14 is substantially semi-circular extending from a flush position with the first or second end of the handle 16 to approximately one-eighth (⅛") inch above the first or second end of the handle 16. The shape of the tongue scraping device 14, as described and shown, allows the tongue scraping device 14 to effectively scrape the tongue at all levels.

Regardless of configuration, the tongue scraping device 14 of the tongue scraper toothbrush system 10 of the present invention is preferably constructed from a plastic material and comprised of a rounded, two prong tongue scraping device 14 having a flat, tapered scraping edge that easily glides over the tongue and collects residue on contact. The toothbrush itself can be offered in a variety of colors and sold in multi-count packages featuring five toothbrushes per unit.

The manner of use of the tongue scraper toothbrush system 10 of the present invention will now be described. It will be understood by those skilled in the art that the manner of use of the tongue scraper toothbrush system 10 described herein is merely one method of use and other methods of use of the tongue scraper toothbrush system 10 are within the scope of the present invention.

Use of the tongue scraper toothbrush system 10 of the present invention is very simple and straightforward. First, users purchase toothbrushes 12 from the line in accordance to bristle preference. The toothbrush 12 is then be utilized in the same manner as any other toothbrush in order to clean the teeth. Squeezing a dollop of favorite toothpaste atop the brush head 18, the user brushes their teeth per usual, making sure to brush the front, back and tops of the teeth completely. Next, the user accesses the integrated tongue scraping device 14 to clean their tongue. Grasping the handle of the toothbrush 12 in hand so that the tongue scraping device 14 is positioned directly over the tongue, the user positions the distal end of the tongue scraping device 14 against the posterior end of the tongue. With gentle but thorough forward strokes, the user effectively removes any residue that can cause bacteria buildup and the resulting halitosis. Once the tongue is scraped clean, the user simply rinses clean the tongue scraping device 14 and brush head 18 of the toothbrush 12, storing the entire toothbrush 12 away until again needed.

There are several benefits and advantages associated with the tongue scraper toothbrush system 10 of the present invention. Foremost, the tongue scraper toothbrush system 10 offers users a simple yet effective tool for brushing the teeth and cleaning the tongue, in one, simple to use unit. An ergonomic toothbrush boasting an integrated tongue scraping device 14 incorporated into its design, the toothbrush 12 ensures that one had all of the implements necessary to ensure proper oral hygiene, in one lightweight and easily employed product. Users appreciate that as the toothbrush 12 has a tongue scraper device 14 incorporated into the toothbrush 12, they will surely remember to scrape their tongue following routine brushing of the teeth, thus ensuring optimal oral health. Further, the tongue scraper toothbrush system 10 not only allows users to ensure proper oral health, but also proves an effective step that ensures confidence in the freshness of their breath. Eradicating germs and bacteria that can cause halitosis from the surface of the tongue, the tongue scraper toothbrush system 10 proves an invaluable commodity in any medicine cabinet. Featuring a compact design that takes up little more space than a traditional toothbrush, the tongue scraper toothbrush system 10 enables the user to store two hygiene tools, without the clutter of conventional scrapers taking up counter space in small, crowded bathrooms. Simple to use, users will appreciate the ease of which the tongue scraper toothbrush system 10 can be employed, with the product ideal for use by adults and children alike.

The tongue scraper toothbrush system 10 of the present invention provides a helpful assist in increasing the number of people who scrape the tongue on a daily basis. Versatile and convenient, the tongue scraper toothbrush system 10 offers a user-friendly approach to healthy oral hygiene that can be easily used by adults and children alike.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein may be suitably practiced in the absence of the specific elements which are disclosed herein.

What is claimed is:

1. A tongue scraper toothbrush system for cleaning the teeth and tongue of a user, the tongue scraper toothbrush system comprising:
   i) a handle having a first end and a second end;
   ii) a slide mechanism;
   iii) a brush head mounted to said first end of said handle;
   iv) a tongue scraping device mounted to said first end of said handle opposite said brush head;

v) wherein said brush head and said tongue scraping device are structured and arranged on said handle for alternatingly cleaning the teeth and the tongue of the user;

vi) wherein said tongue scraping device is comprised of a pair of elongate, arcuately curved prongs, each prong having a flat, tapered scraping edge and an upper edge surface;

vii) each of the elongate, curved prongs of the tongue scraper device being oriented such that they are aligned with the longitudinal axis of the handle; and viii) wherein the tongue scraping device is operatively engaged with the slide mechanism such that the prongs thereof can move between a non-use position in which the upper edge surface of the prongs are flush with an adjacent surface of the handle and a use position in which the upper edge surface of the prongs are raised so as to be spaced above the adjacent surface of the handle.

2. The tongue scraper toothbrush system of claim 1 wherein said brush head has a plurality of bristles.

3. The tongue scraper toothbrush system of claim 2 wherein said bristles have rounded edges.

4. The tongue scraper toothbrush system of claim 1 wherein said handle is ergonomic shaped.

5. The tongue scraper toothbrush system of claim 1 and further comprising:

i) a nonskid grip mounted to said handle.

\* \* \* \* \*